(12) United States Patent
Fleming et al.

(10) Patent No.: US 8,070,046 B1
(45) Date of Patent: *Dec. 6, 2011

(54) AMINE FLUX COMPOSITION AND METHOD OF SOLDERING

(75) Inventors: David D. Fleming, Northborough, MA (US); Mike K. Gallagher, Hopkinton, MA (US); Kim Sang Ho, Richboro, PA (US); Xiang-Qian Liu, Collegeville, PA (US); Mark R. Winkle, Lansdale, PA (US); Asghar Akber Peera, Cary, IL (US); Glenn N. Robinson, Naperville, IL (US); Ian Tomlinson, Midland, MI (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/958,493

(22) Filed: Dec. 2, 2010

(51) Int. Cl.
*B23K 31/02* (2006.01)
*B23K 35/34* (2006.01)

(52) U.S. Cl. ............... 228/180.21; 228/207; 228/223; 228/224; 228/248.1; 148/23; 148/24

(58) Field of Classification Search .................. None
See application file for complete search history.

(56) References Cited

U.S. PATENT DOCUMENTS

| | | | |
|---|---|---|---|
| 2,632,022 A | 3/1959 | Bortnick | |
| 2,897,179 A | 7/1959 | Schecter et al. | |
| 3,488,831 A * | 1/1970 | Ravve | 228/199 |
| 3,740,831 A * | 6/1973 | Jordan et al. | 228/223 |
| 3,814,638 A * | 6/1974 | Warwick et al. | 148/23 |
| 4,028,143 A * | 6/1977 | Stayner et al. | 148/23 |
| 4,165,244 A * | 8/1979 | Jacobs | 148/23 |
| 4,196,024 A * | 4/1980 | Kenyon | 148/23 |
| 4,360,144 A * | 11/1982 | Cuddy et al. | 228/180.1 |
| RE32,309 E * | 12/1986 | Hwang | 148/23 |
| 5,011,546 A * | 4/1991 | Frazier et al. | 148/23 |
| 5,041,169 A * | 8/1991 | Oddy et al. | 148/23 |
| 5,145,722 A * | 9/1992 | Kaspaul | 427/388.1 |
| 5,256,209 A * | 10/1993 | Chihara et al. | 134/38 |
| 5,531,838 A | 7/1996 | Arldt et al. | |
| 5,571,340 A | 11/1996 | Schneider et al. | |
| 5,599,894 A * | 2/1997 | Ikeno | 528/15 |
| 5,863,355 A * | 1/1999 | Ohno et al. | 148/26 |
| 5,932,030 A * | 8/1999 | Fukasawa et al. | 148/23 |
| 5,958,151 A | 9/1999 | Gao et al. | |
| 5,981,682 A * | 11/1999 | Onishi | 528/31 |
| 5,989,362 A | 11/1999 | Diamant et al. | |
| 6,063,898 A * | 5/2000 | Endo et al. | 528/411 |
| 6,217,671 B1 | 4/2001 | Henderson et al. | |
| 6,234,381 B1 * | 5/2001 | Hasegawa et al. | 228/223 |
| 6,283,360 B1 * | 9/2001 | Kumai et al. | 228/209 |
| 6,367,150 B1 | 4/2002 | Kirsten | |
| 6,667,194 B1 * | 12/2003 | Crane et al. | 438/127 |
| 6,758,389 B1 * | 7/2004 | Odaka et al. | 228/207 |
| 6,887,319 B2 * | 5/2005 | Suga et al. | 148/23 |
| 6,926,849 B2 * | 8/2005 | Taguchi et al. | 252/512 |
| 7,009,009 B1 * | 3/2006 | Crane et al. | 525/533 |
| 7,575,150 B2 | 8/2009 | Saito et al. | |
| 2001/0019075 A1 * | 9/2001 | Abe et al. | 228/224 |
| 2001/0045244 A1 * | 11/2001 | Akaike et al. | 148/25 |
| 2002/0089067 A1 * | 7/2002 | Crane et al. | 257/778 |
| 2002/0190370 A1 * | 12/2002 | Shi et al. | 257/690 |
| 2003/0032729 A1 * | 2/2003 | Takai et al. | 525/107 |
| 2003/0073770 A1 * | 4/2003 | Klemarczyk et al. | 524/404 |
| 2003/0111519 A1 * | 6/2003 | Kinney et al. | 228/223 |
| 2003/0159761 A1 * | 8/2003 | Ikeda et al. | 148/24 |
| 2004/0122208 A1 * | 6/2004 | Okada | 528/408 |
| 2005/0048291 A1 * | 3/2005 | Woo et al. | 428/413 |
| 2005/0048700 A1 * | 3/2005 | Rubinsztajn et al. | 438/127 |
| 2005/0049334 A1 * | 3/2005 | Rubinsztain et al. | 523/456 |
| 2005/0067395 A1 | 3/2005 | Shindo et al. | |
| 2005/0129956 A1 * | 6/2005 | Rubinsztajn et al. | 428/413 |
| 2005/0131106 A1 * | 6/2005 | Tonapi et al. | 523/216 |
| 2005/0170188 A1 * | 8/2005 | Campbell et al. | 428/413 |
| 2005/0181214 A1 * | 8/2005 | Campbell et al. | 428/413 |
| 2005/0266263 A1 * | 12/2005 | Campbell et al. | 428/624 |
| 2005/0288458 A1 * | 12/2005 | Klemarczyk et al. | 525/533 |
| 2006/0020068 A1 * | 1/2006 | Elce et al. | 524/356 |

(Continued)

OTHER PUBLICATIONS

STIC search, no date available.*

(Continued)

*Primary Examiner* — Kiley Stoner
(74) *Attorney, Agent, or Firm* — Thomas S. Deibert

(57) ABSTRACT

An amine flux composition is provided, comprising, as an initial component: an amine fluxing agent represented by formula I:

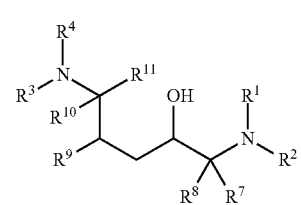

(I)

wherein $R^1$, $R^2$, $R^3$ and $R^4$ are independently selected from a hydrogen, a substituted $C_{1-80}$ alkyl group, an unsubstituted $C_{1-80}$ alkyl group, a substituted $C_{7-80}$ arylalkyl group and an unsubstituted $C_{7-80}$ arylalkyl group; wherein $R^7$ and $R^8$ are independently selected from a $C_{1-20}$ alkyl group, a substituted $C_{1-20}$ alkyl group, a $C_{6-20}$ aryl group and a substituted $C_{6-20}$ aryl group or wherein $R^7$ and $R^8$, together with the carbon to which they are attached, form a $C_{3-20}$ cycloalkyl ring optionally substituted with a $C_{1-6}$ alkyl group; wherein $R^{10}$ and $R^{11}$ are independently selected from a $C_{1-20}$ alkyl group, a substituted $C_{1-20}$ alkyl group, a $C_{6-20}$ aryl group and a substituted $C_{6-20}$ aryl group or wherein $R^{10}$ and $R^{11}$, together with the carbon to which they are attached, form a $C_{3-20}$ cycloalkyl ring optionally substituted with a $C_{1-6}$ alkyl group; and, wherein $R^9$ is selected from a hydrogen, a $C_{1-30}$ alkyl group, a substituted $C_{1-30}$ alkyl group, a $C_{6-30}$ aryl group and a substituted $C_{6-30}$ aryl group. Also provided is a method of soldering an electrical contact using the amine flux composition.

10 Claims, No Drawings

U.S. PATENT DOCUMENTS

| | | | |
|---|---|---|---|
| 2006/0102691 A1* | 5/2006 | Toyama et al. | 228/101 |
| 2006/0147683 A1* | 7/2006 | Ikeda et al. | 428/209 |
| 2006/0147719 A1* | 7/2006 | Rubinsztajn et al. | 428/413 |
| 2006/0192280 A1* | 8/2006 | Esler et al. | 257/701 |
| 2006/0219757 A1* | 10/2006 | Rubinsztajn | 228/101 |
| 2006/0272747 A1 | 12/2006 | Wang et al. | |
| 2006/0275608 A1* | 12/2006 | Tonapi et al. | 428/413 |
| 2006/0275952 A1* | 12/2006 | Gowda et al. | 438/122 |
| 2007/0104959 A1* | 5/2007 | Asano et al. | 428/413 |
| 2007/0186997 A1* | 8/2007 | Ikeda et al. | 148/23 |
| 2007/0241170 A1* | 10/2007 | Ikeda et al. | 228/224 |
| 2007/0277373 A1 | 12/2007 | Takai et al. | |
| 2007/0281097 A1* | 12/2007 | Ikeno et al. | 427/387 |
| 2008/0023108 A1 | 1/2008 | Wang et al. | |
| 2008/0039542 A1* | 2/2008 | Mills et al. | 522/31 |
| 2008/0039560 A1* | 2/2008 | Mills et al. | 524/183 |
| 2008/0050552 A1* | 2/2008 | Ahn et al. | 428/98 |
| 2008/0066830 A1* | 3/2008 | Gunji et al. | 148/23 |
| 2008/0113297 A1* | 5/2008 | Shibasaki et al. | 430/286.1 |
| 2008/0124568 A1* | 5/2008 | Duchesne et al. | 428/615 |
| 2008/0156852 A1* | 7/2008 | Prakash | 228/256 |
| 2008/0179383 A1* | 7/2008 | Sakurai et al. | 228/208 |
| 2008/0214840 A1* | 9/2008 | Klemarczyk et al. | 549/90 |
| 2009/0018239 A1* | 1/2009 | Woods et al. | 523/459 |
| 2009/0123642 A1* | 5/2009 | Sato | 427/98.5 |
| 2009/0194319 A1* | 8/2009 | Itoh et al. | 174/250 |
| 2010/0041803 A1* | 2/2010 | Dershem | 524/219 |
| 2010/0041823 A1* | 2/2010 | Dershem | 524/588 |
| 2010/0041832 A1* | 2/2010 | Dershem | 525/208 |
| 2010/0143658 A1 | 6/2010 | Lawrence | |
| 2010/0175790 A1 | 7/2010 | Duchesne et al. | |
| 2011/0100512 A1* | 5/2011 | Bedard et al. | 148/240 |
| 2011/0152466 A1* | 6/2011 | Dershem | 525/329.3 |
| 2011/0177242 A1* | 7/2011 | Kolowrot et al. | 427/207.1 |

OTHER PUBLICATIONS

Copending U.S. Appl. No. 12/958,495.
Copending U.S. Appl. No. 12/958,487.
Copending U.S. Appl. No. 12/958,480.
Copending U.S. Appl. No. 12/958,473.

* cited by examiner

AMINE FLUX COMPOSITION AND METHOD OF SOLDERING

The present invention relates to an amine flux composition comprising, as an initial component an amine fluxing agent represented by formula I, wherein $R^1$, $R^2$, $R^3$ and $R^4$ are independently selected from a hydrogen, a substituted $C_{1-80}$ alkyl group, an unsubstituted $C_{1-80}$ alkyl group, a substituted $C_{7-80}$ arylalkyl group and an unsubstituted $C_{7-80}$ arylalkyl group; wherein $R^7$ and $R^8$ are independently selected from a $C_{1-20}$ alkyl group, a substituted $C_{1-20}$ alkyl group, a $C_{6-20}$ aryl group and a substituted $C_{6-20}$ aryl group or wherein $R^7$ and $R^8$, together with the carbon to which they are attached, form a $C_{3-20}$ cycloalkyl ring optionally substituted with a $C_{1-6}$ alkyl group; wherein $R^{10}$ and $R^{11}$ are independently selected from a $C_{1-20}$ alkyl group, a substituted $C_{1-20}$ alkyl group, a $C_{6-20}$ aryl group and a substituted $C_{6-20}$ aryl group or wherein $R^{10}$ and $R^{11}$, together with the carbon to which they are attached, form a $C_{3-20}$ cycloalkyl ring optionally substituted with a $C_{1-6}$ alkyl group; and, wherein $R^9$ is selected from a hydrogen, a $C_{1-30}$ alkyl group, a substituted $C_{1-30}$ alkyl group, a $C_{6-30}$ aryl group and a substituted $C_{6-30}$ aryl group. The present invention further relates to a method of soldering an electrical contact.

Soldering processes ranging from manual, hand soldering methods to automated soldering methods. The use of flux materials in soldering processes, both manual and automated, is also well know. In fact, the use of solder alone generally will not result in an acceptable electrical interconnection. Flux materials serve multiple functions in the soldering process. For example, flux materials operate to remove any oxides that may have formed on the metallic contacts (e.g., solder regions, contact pads, contact pins, copper plated through holes); to enhance wetting of solder onto the metallic contacts.

Various methods have been employed to apply flux materials to the surface of a metallic contact during the soldering process. In some methods, flux materials containing solder are used. For example, such combined materials have been provided in the form of an annular shaped wire incorporating a core of flux material. As the solder melts upon heating, the flux material in the core is activated, fluxing the surfaces to be interconnected by the molten solder. Solder pastes are also known in which a flux material and a solder powder are compounded to form a generally homogenous stable suspension of solder particles in the paste.

One commercially significant, application of an automated soldering method is the manufacture of semiconductor devices. That is, reflow soldering processes are commonly used in the automated production of semiconductor devices, wherein a semiconductor chip is mounted on to a printed circuit board (PCB). In some such automated production methods, a solder paste is applied to a printed circuit board using, for example, screen printing or stencil printing. The semiconductor chip is then brought into contact with the PCB and the solder paste is heated to reflow the solder in the paste, forming electrical interconnects between the semiconductor chip and the PCB. The heating may be facilitated by, for example, exposure of the solder paste to infrared light or by heating in an oven. In some applications, the semiconductor chip/PCB assembly is further treated with an under fill material that substantially fills the interstitial area between the semiconductor chip and the PCB, encapsulating the interconnects.

Given the demands for the mass production of electronic devices containing circuits of increasing complexity and miniaturization, rapid, automated soldering processes have emerged, such as, for example, those incorporating pick and dip processes. In such processes, a flux can be applied to a plurality of electrical contacts on a semiconductor chip by dipping the electrical contact portion of the semiconductor chip into a bath of flux. The flux coated electrical contacts on the semiconductor chip can then be brought into contact with a PCB comprising corresponding electrical contacts and solder balls. The solder balls may then be heated to reflux interconnecting the semiconductor chip and the PCB. Alternatively, the pick and dip process can be employed with device components that have electrical contacts with preapplied solder. In these processes, the preapplied solder is dip coated with the flux material and then brought into contact with the corresponding electrical contact(s) and heated to reflow, forming the electrical interconnects. Many electronic components fit into this latter process category in that they are manufactured with a sufficient amount of solder on board the component to facilitate interconnection of the component with another electrical component (e.g., a PCB).

In most instances, use of commercially available fluxes leave ionic residues on the soldered regions, which may undesirably lead to corrosion of circuitry and to short circuits. Accordingly, additional process steps are required to remove such residues after formation of the soldered interconnections. For semiconductor device manufacturing processes, the solder connections formed between the semiconductor chip and the PCB result in a relatively small gap between the semiconductor chip and the PCB (e.g., <4 mils). Hence, it is very difficult to remove (i.e., clean) ionic residues remaining on the soldered regions following the soldering process. Even in processes where the soldered regions are accessible (hence, facilitating cleaning operations), cleaning operations create environmental concerns involving the disposal of the waste generated during the cleaning operations.

Some low residue, no clean fluxes having a low solid content are commercially available. One flux composition asserted to substantially minimize or substantially eliminate flux residues when soldering electronic components is disclosed in United States Patent Application Publication No. 20100175790 to Duchesne et al. Duchesne et al. disclose a composition of matter comprising a flux, wherein said flux consists essentially of a combination of: (a) a fluxing agent; and (b) a solvent; wherein said fluxing agent: (1) comprises a keto acid; or (2) comprises an ester acid; or (3) comprises a mixture of said keto acid with said ester acid; and wherein said solvent comprises a mixture of a tacky solvent selected from polyhydric alcohols or mixtures thereof, and a non-tacky solvent selected from monohydric alcohols or mixtures thereof.

Notwithstanding, there remains a need for flux compositions that are non-curing, facilitate reliable soldering connections and are customizable to facilitate compatibility with conventional epoxy based under fill materials.

The present invention provides an amine flux composition comprising, as an initial component: an amine fluxing agent represented by formula I:

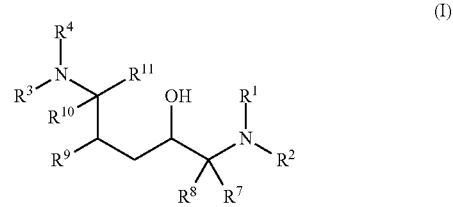

wherein $R^1$, $R^2$, $R^3$ and $R^4$ are independently selected from a hydrogen, a substituted $C_{1-80}$ alkyl group, an unsubstituted $C_{1-80}$ alkyl group, a substituted $C_{7-80}$ arylalkyl group and an unsubstituted $C_{7-80}$ arylalkyl group; wherein $R^7$ and $R^8$ are independently selected from a $C_{1-20}$ alkyl group, a substituted $C_{1-20}$ alkyl group, a $C_{6-20}$ aryl group and a substituted $C_{6-20}$ aryl group or wherein $R^7$ and $R^8$, together with the carbon to which they are attached, form a $C_{3-20}$ cycloalkyl ring optionally substituted with a $C_{1-6}$ alkyl group; wherein $R^{10}$ and $R^{11}$ are independently selected from a $C_{1-20}$ alkyl group, a substituted $C_{1-20}$ alkyl group, a $C_{6-20}$ aryl group and a substituted $C_{6-20}$ aryl group or wherein $R^{10}$ and $R^{11}$, together with the carbon to which they are attached, form a $C_{3-20}$ cycloalkyl ring optionally substituted with a $C_{1-6}$ alkyl group; and, wherein $R^9$ is selected from a hydrogen, a $C_{1-30}$ alkyl group, a substituted $C_{1-30}$ alkyl group, a $C_{6-30}$ aryl group and a substituted $C_{6-30}$ aryl group.

The present invention provides a method of applying solder to an electrical contact, comprising: providing an electrical contact; providing an amine flux composition of the present invention; applying the amine flux composition to the electrical contact; providing a solder; melting the solder; and, displacing the amine flux composition applied to the electrical contact with the molten solder; wherein the molten solder makes physical contact with the electrical contact and bonds to the electrical contact.

DETAILED DESCRIPTION

The amine flux composition of the present invention is designed to facilitate compatibilization with various under fill compositions, such that, the soldered surfaces preferably do not require cleaning before application of an under fill composition to form a finished electrical joint.

The term "no clean flux composition" as used herein and in the appended claims refers to amine flux compositions that exhibit a low, or no, amine flux residue activity with <0.5 wt % halide content (i.e., amine fluxes that are categorized as an ORL1 or ORL0 under IPC J-STD-004B).

The amine flux composition of the present invention comprises (consists essentially of), as an initial component: an amine fluxing agent represented by formula I. Preferably, the amine flux composition is a non-curing composition (i.e., wherein the amine flux composition is free of compounds having two or more reactive functional groups per molecule capable of reacting under soldering conditions to form inter molecular covalent bonds and wherein the amine fluxing agent does not contain two or more reactive functional groups per molecule capable of reacting under soldering conditions to form inter molecular covalent bonds).

The amine fluxing agent used in the amine flux composition of the present invention is according to formula I, wherein $R^1$, $R^2$, $R^3$ and $R^4$ are independently selected from hydrogen, a substituted $C_{1-80}$ alkyl group, an unsubstituted $C_{1-80}$ alkyl group, a substituted $C_{7-80}$ arylalkyl group and an unsubstituted $C_{7-80}$ arylalkyl group (preferably wherein $R^1$, $R^2$, $R^3$ and $R^4$ are independently selected from a hydrogen, a substituted $C_{1-20}$ alkyl group, an unsubstituted $C_{1-20}$ alkyl group, a substituted $C_{7-30}$ arylalkyl group and an unsubstituted $C_{7-30}$ arylalkyl group); wherein $R^7$ and $R^8$ are independently selected from a $C_{1-20}$ alkyl group, a substituted $C_{1-20}$ alkyl group, a $C_{6-20}$ aryl group and a substituted $C_{6-20}$ aryl group (alternatively, wherein $R^7$ and $R^8$, together with the carbon to which they are attached, form a $C_{3-20}$ cycloalkyl ring optionally substituted with a $C_{1-6}$ alkyl group); wherein $R^{10}$ and $R^{11}$ are independently selected from a $C_{1-20}$ alkyl group, a substituted $C_{1-20}$ alkyl group, a $C_{6-20}$ aryl group and a substituted $C_{6-20}$ aryl group (alternatively, wherein $R^{10}$ and $R^{11}$, together with the carbon to which they are attached, form a $C_{3-20}$ cycloalkyl ring optionally substituted with a $C_{1-6}$ alkyl group); and, wherein $R^9$ is selected from a hydrogen, a $C_{1-30}$ alkyl group, a substituted $C_{1-30}$ alkyl group, a $C_{6-30}$ aryl group and a substituted $C_{6-30}$ aryl group. Preferably, zero to three of $R^1$, $R^2$, $R^3$ and $R^4$ is(are) hydrogen. The $R^1$, $R^2$, $R^3$, $R^4$, $R^7$, $R^8$, $R^9$, $R^{10}$ and $R^{11}$ groups of the amine fluxing agent according to formula I are preferably selected: to provide the amine fluxing agent with desirable rheological properties for a given application; optionally, to compatibilize the amine fluxing agent with a given solvent package for delivery to the surface(s) to be soldered; and, optionally, to compatibilize the amine fluxing agent with a given encapsulating composition (e.g., an epoxy resin) to be used post soldering to form an encapsulated solder joint (e.g., for use in conventional flip chip under fill applications). Preferably, the $R^1$, $R^2$, $R^3$, $R^4$, $R^7$, $R^8$, $R^9$, $R^{10}$ and $R^{11}$ groups of the amine fluxing agent according to formula I are selected to compatibilize the amine fluxing agent with a given encapsulating composition such that the amine flux composition is a no clean flux composition. Preferably, zero to three of $R^1$, $R^2$, $R^3$ and $R^4$ is(are) hydrogen. More preferably, one to three of $R^1$, $R^2$, $R^3$ and $R^4$ is(are) hydrogen. Still more preferably, two to three of $R^1$,$R^2$, $R^3$ and $R^4$ are hydrogen. Yet still more preferably, two of $R^1$, $R^2$, $R^3$ and $R^4$ are hydrogen. Most preferably, one of $R^1$ and $R^2$ is hydrogen and one of $R^3$ and $R^4$ is hydrogen. Also, the $R^1$, $R^2$, $R^3$, $R^4$, $R^7$, $R^8$, $R^9$, $R^{10}$ and $R^{11}$ groups of the amine fluxing agent according to formula I are preferably selected to provide the amine fluxing agent with a boiling point temperature, determined by differential scanning calorimetry of $\geq$ 125° C. (more preferably $\geq$250° C.) and a percent weight loss of $\leq$10 wt % upon heating to 250° C. determined by thermogravimetric analysis (TGA) using a temperature ramp of 10° C./min starting at 25° C.

Preferably, the amine fluxing agent used in the amine fluxing composition of the present invention is according to formula I; wherein $R^1$, $R^2$, $R^3$ and $R^4$ are independently selected from a hydrogen, a substituted $C_{1-80}$ alkyl group, an unsubstituted $C_{1-80}$ alkyl group, a substituted $C_{7-80}$ arylalkyl group and an unsubstituted $C_{7-80}$ arylalkyl group; and, wherein the substitutions in the substituted $C_{1-80}$ alkyl group and the substituted $C_{7-80}$ arylalkyl group are selected from at least one of an —OH group, an —OR$^5$ group, a —COR$^5$— group, a —COR$^5$ group, a —C(O)R$^5$ group, a —CHO group, a —COOR$^5$ group, an —OC(O)OR$^5$ group, a —S(O)(O)R$^5$ group, a —S(O)R$^5$ group, a —S(O)(O)NR$^5{}_2$ group, an —OC(O)NR$^6{}_2$ group, a —C(O)NR$^6{}_2$ group, a —CN group, a —N(R$^6$)— group and a —NO$_2$ group (preferably at least one of an —OH group, an —OR$^5$ group, a —COR$^5$— group, a —COR$^5$ group, a —C(O)R$^5$ group, a —CHO group, a —COOR$^5$ group, an —OC(O)OR$^5$ group, a —S(O)(O)R$^5$ group, a —S(O)R$^5$ group, a —S(O)(O)NR$^5{}_2$ group, an —OC(O)NR$^6{}_2$ group, a —C(O)NR$^6{}_2$ group, a —CN group and a —NO$_2$ group); wherein R$^5$ is selected from a $C_{1-28}$ alkyl group, a $C_{3-28}$ cycloalkyl group, a $C_{6-15}$ aryl group, a $C_{7-28}$ arylalkyl group and a $C_{7-28}$ alkylaryl group; wherein R$^6$ is selected from a hydrogen, a $C_{1-28}$ alkyl group, a $C_{3-28}$ cycloalkyl group, a $C_{6-15}$ aryl group, a $C_{7-28}$ arylalkyl group and a $C_{7-28}$ alkylaryl group. The substituted $C_{1-80}$ alkyl group and the substituted $C_{7-80}$ arylalkyl group can contain combinations of substitutions. For example, the substituted $C_{1-80}$ alkyl group and the substituted $C_{7-80}$ arylalkyl group can: contain more than one of the same type of substitution (e.g., two —OH groups); contain more than one type of substitution (e.g., an —OH group and a —COR$^5$— group); contain more than one type of substitution with more than one of the same type of substitution (e.g., two —OH groups and an —OR$^5$ group).

Preferably, the amine fluxing agent used in the amine fluxing composition of the present invention is according to formula I; wherein R$^7$ and R$^8$ are independently selected from a C$_{1-20}$ alkyl group, a substituted C$_{1-20}$ alkyl group, a C$_{6-20}$ aryl group and a substituted C$_{6-20}$ aryl group (alternatively, wherein R$^7$ and R$^8$, together with the carbon to which they are attached, form a C$_{3-20}$ cycloalkyl ring optionally substituted with a C$_{1-6}$ alkyl group); and wherein the substitutions in the substituted C$_{1-20}$ alkyl group and the substituted C$_{6-20}$ aryl group are selected from at least one of an —OH group, a phenyl group, a C$_{1-14}$ alkyl group, an —OR$^{12}$ group, a —COR$^{12}$— group, a —COR$^{12}$ group, a —C(O)R$^{12}$ group, a —CHO group, a —COOR$^{12}$ group, an —OC(O)OR$^{12}$ group, a —S(O)(O)R$^{12}$ group, a —S(O)R$^{12}$ group, a —S(O)(O)NR$^{13}{}_2$ group, an —OC(O)NR$^{13}{}_2$ group, a —C(O)NR$^{13}{}_2$ group, a —CN group, a —N(R$^{13}$)— group and a —NO$_2$ group (preferably at least one of an —OH group, an —OR$^{12}$ group, a —COR$^{12}$— group, a —COR$^{12}$ group, a —C(O)R$^{12}$ group, a —CHO group, a —COOR$^{12}$ group, an —OC(O)OR$^{12}$ group, a —S(O)(O)R$^{12}$ group, a —S(O)R$^{12}$ group, a —S(O)(O)NR$^{12}{}_2$ group, an —OC(O)NR$^{13}{}_2$ group, a —C(O)NR$^{13}{}_2$ group, a —CN group and a —NO$_2$ group); wherein R$^{12}$ is selected from a C$_{1-19}$ alkyl group, a C$_{3-19}$ cycloalkyl group, a C$_{6-19}$ aryl group, a C$_{7-19}$ arylalkyl group and a C$_{7-19}$ alkylaryl group; and wherein R$^{13}$ is selected from a hydrogen, a C$_{1-19}$ alkyl group, a C$_{3-19}$ cycloalkyl group, a C$_{6-19}$ aryl group, a C$_{7-19}$ arylalkyl group and a C$_{7-19}$ alkylaryl group. The substituted C$_{1-20}$ alkyl group and the substituted C$_{6-20}$ aryl group can contain combinations of substitutions. For example, the substituted C$_{1-20}$ alkyl group and the substituted C$_{6-20}$ aryl group can: contain more than one of the same type of substitution (e.g., two —OH groups); contain more than one type of substitution (e.g., an —OH group and a —COR$^{12}$— group); contain more than one type of substitution with more than one of the same type of substitution (e.g., two —OH groups and an —OR$^{12}$ group).

Preferably, the amine fluxing agent used in the amine fluxing composition of the present invention is according to formula I; wherein R$^{10}$ and R$^{11}$ are independently selected from a C$_{1-20}$ alkyl group, a substituted C$_{1-20}$ alkyl group, a C$_{6-20}$ aryl group and a substituted C$_{6-20}$ aryl group (alternatively, wherein R$^{10}$ and R$^{11}$, together with the carbon to which they are attached, form a C$_{3-20}$ cycloalkyl ring optionally substituted with a C$_{1-6}$ alkyl group); and, wherein the substitutions in the substituted C$_{1-20}$ alkyl group and the substituted C$_{6-20}$ aryl group are selected from at least one of an —OH group, an —OR$^{12}$ group, a —COR$^{12}$— group, a —COR$^{12}$ group, a —C(O)R$^{12}$ group, a —CHO group, a —COOR$^{12}$ group, an —OC(O)OR$^{12}$ group, a —S(O)(O)R$^{12}$ group, a —S(O)R$^{12}$ group, a —S(O)(O)NR$^{12}{}_2$ group, an —OC(O)NR$^{13}{}_2$ group, a —C(O)NR$^{13}{}_2$ group, a —CN group, a —N(R$^{13}$)— group and a —NO$_2$ group (preferably at least one of an —OH group, an —OR$^{12}$ group, a —COR$^{12}$— group, a —COR$^{12}$ group, a —C(O)R$^{12}$ group, a —CHO group, a —COOR$^{12}$ group, an —OC(O)OR$^{12}$ group, a —S(O)(O)R$^{12}$ group, a —S(O)R$^{12}$ group, a —S(O)(O)NR$^{12}{}_2$ group, an —OC(O)NR$^{13}{}_2$ group, a —C(O)NR$^{13}{}_2$ group, a —CN group and a —NO$_2$ group); wherein R$^{12}$ is selected from a C$_{1-19}$ alkyl group, a C$_{3-19}$ cycloalkyl group, a C$_{6-19}$ aryl group, a C$_{7-19}$ arylalkyl group and a C$_{7-19}$ alkylaryl group; and wherein R$^{13}$ is selected from a hydrogen, a C$_{1-19}$ alkyl group, a C$_{3-19}$ cycloalkyl group, a C$_{6-19}$ aryl group, a C$_{7-19}$ arylalkyl group and a C$_{7-19}$ alkylaryl group. The substituted C$_{1-20}$ alkyl group and the substituted C$_{6-20}$ aryl group can contain combinations of substitutions. For example, the substituted C$_{1-20}$ alkyl group and the substituted C$_{6-20}$ aryl group can: contain more than one of the same type of substitution (e.g., two —OH groups); contain more than one type of substitution (e.g., an —OH group and a —COR$^{12}$— group); contain more than one type of substitution with more than one of the same type of substitution (e.g., two —OH groups and an —OR$^{12}$ group).

Preferably, the amine fluxing agent used in the amine fluxing composition of the present invention is according to formula I; wherein R$^9$ is selected from a hydrogen, a C$_{1-30}$ alkyl group, a substituted C$_{1-30}$ alkyl group, a C$_{6-30}$ aryl group and a substituted C$_{6-30}$ aryl group; and, wherein the substitutions in the substituted C$_{1-30}$ alkyl group and the substituted C$_{6-30}$ aryl group are selected from at least one of an —OH group, an —OR$^{14}$ group, a —COR$^{14}$— group, a —COR$^{14}$ group, a —C(O)R$^{14}$ group, a —CHO group, a —COOR$^{14}$ group, an —OC(O)OR$^{14}$ group, a —S(O)(O)R$^{14}$ group, a —S(O)R$^{14}$ group, a —S(O)(O)NR$^{14}{}_2$ group, an —OC(O)NR$^{15}{}_2$ group, a —C(O)NR$^{15}{}_2$ group, a —CN group, a —N(R$^{15}$)— group and a —NO$_2$ group (preferably at least one of an —OH group, an —OR$^{14}$ group, a —COR$^{14}$— group, a —COR$^{14}$ group, a —C(O)R$^{14}$ group, a —CHO group, a —COOR$^{14}$ group, an —OC(O)OR$^{14}$ group, a —S(O)(O)R$^{14}$ group, a —S(O)R$^{14}$ group, a —S(O)(O)NR$^{14}{}_2$ group, an —OC(O)NR$^{15}{}_2$ group, a —C(O)NR$^{15}{}_2$ group, a —CN group and a —NO$_2$ group); wherein R$^{14}$ is selected from a C$_{1-29}$ alkyl group, a C$_{3-29}$ cycloalkyl group, a C$_{6-29}$ aryl group, a C$_{7-29}$ arylalkyl group and a C$_{7-29}$ alkylaryl group; and wherein R$^{15}$ is selected from a hydrogen, a C$_{1-29}$ alkyl group, a C$_{3-29}$ cycloalkyl group, a C$_{6-29}$ aryl group, a C$_{7-29}$ arylalkyl group and a C$_{7-29}$ alkylaryl group. The substituted C$_{1-30}$ alkyl group and the substituted C$_{6-30}$ aryl group can contain combinations of substitutions. For example, the substituted C$_{1-30}$ alkyl group and the substituted C$_{6-30}$ aryl group can: contain more than one of the same type of substitution (e.g., two —OH groups); contain more than one type of substitution (e.g., an —OH group and a —COR$^{14}$— group); contain more than one type of substitution with more than one of the same type of substitution (e.g., two —OH groups and an —OR$^{14}$ group).

More preferably, the amine fluxing agent used in the amine fluxing composition of the present invention is according to formula I; wherein R$^1$, R$^2$, R$^3$ and R$^4$ are independently selected from a hydrogen, a substituted C$_{1-20}$ alkyl group, an unsubstituted C$_{1-20}$ alkyl group, a substituted C$_{7-30}$ arylalkyl group and an unsubstituted C$_{7-30}$ arylalkyl group; and, wherein the substitutions in the substituted C$_{1-20}$ alkyl group and the substituted C$_{7-30}$ arylalkyl group are selected from at least one of an —OH group, an —OR$^{16}$ group, a —COR$^{16}$— group, a —COR$^{16}$ group, a —C(O)R$^{16}$ group, a —CHO group, a —COOR$^{16}$ group, an —OC(O)OR$^{16}$ group, a —S(O)(O)R$^{16}$ group, a —S(O)R$^{16}$ group, a —S(O)(O)NR$^{16}{}_2$ group, an —OC(O)NR$^{17}{}_2$ group, a —C(O)NR$^{17}{}_2$ group, a —CN group, a —N(R$^{17}$)— group and a —NO$_2$ group (preferably at least one of an —OH group, an —OR$^{16}$ group, a —COR$^{16}$— group, a —COR$^{16}$ group, a —C(O)R$^{16}$ group, a —CHO group, a —COOR$^{16}$ group, an —OC(O)OR$^{16}$ group, a —S(O)(O)R$^{16}$ group, a —S(O)R$^{16}$ group, a —S(O)(O)NR$^{16}{}_2$ group, an —OC(O)NR$^{17}{}_2$ group, a —C(O)NR$^{17}{}_2$ group, a —CN group and a —NO$_2$ group); wherein R$^{16}$ is selected from a C$_{1-19}$ alkyl group, a C$_{3-19}$ cycloalkyl group, a C$_{6-15}$ aryl group, a C$_{7-19}$ arylalkyl group and a C$_{7-19}$ alkylaryl group; wherein R$^{17}$ is selected from a hydrogen, a C$_{1-19}$ alkyl group, a C$_{3-19}$ cycloalkyl group, a C$_{6-15}$ aryl group, a C$_{7-19}$ arylalkyl group and a C$_{7-19}$ alkylaryl group; wherein R$^7$ and R$^8$ are independently selected from a C$_{1-4}$ alkyl group and a C$_{1-4}$ hydroxy alkyl group (more preferably wherein R$^7$ and R$^8$ are independently selected from a methyl group and a hydroxy methyl group; most preferably wherein $R^7$ and $R^8$ are both a methyl group); wherein $R^{10}$ and $R^{11}$ are independently selected from a $C_{1-4}$ alkyl group and a $C_{1-4}$ hydroxy alkyl group (more preferably wherein $R^{10}$ and $R^{11}$ are independently selected from a methyl group and a hydroxy methyl group; most preferably wherein $R^{10}$ and $R^{11}$ are both a methyl group); and, wherein $R^9$ is selected from a hydrogen, a $C_{1-10}$ alkyl group, a $C_{1-10}$ hydroxyalkyl group, a phenyl group, a hydroxyphenyl group, a $C_{7-10}$ alkylaryl group, a $C_{7-10}$ arylalkyl group and a naphthyl group (more preferably wherein $R^9$ is selected from a hydrogen, a $C_{1-4}$ alkyl group, a $C_{1-4}$ hydroxyl alkyl group, a phenyl group, a hydroxyl phenyl group, a $C_7$ alkylaryl group and a $C_7$ arylalkyl group; most preferably wherein $R^9$ is selected from a methyl group and a phenyl group). The substituted $C_{1-20}$ alkyl group and the substituted $C_{7-30}$ arylalkyl group, from which $R^1$, $R^2$, $R^3$ and $R^4$ are selected, can contain combinations of substitutions. For example, the substituted $C_{1-20}$ alkyl group and the substituted $C_{7-30}$ arylalkyl group can: contain more than one of the same type of substitution (e.g., two —OH groups); contain more than one type of substitution (e.g., an —OH group and a —$COR^{16}$- group); contain more than one type of substitution with more than one of the same type of substitution (e.g., two —OH groups and an —$OR^{16}$ group). Preferably, zero to three of $R^1$, $R^2$, $R^3$ and $R^4$ is(are) hydrogen. More preferably, one to three of $R^1$, $R^2$, $R^3$ and $R^4$ is(are) hydrogen. Still more preferably, two to three of $R^1$, $R^2$, $R^3$ and $R^4$ are hydrogen. Yet still more preferably, two of $R^1$, $R^2$, $R^3$ and $R^4$ are hydrogen. Most preferably, one of $R^1$ and $R^2$ is hydrogen and one of $R^3$ and $R^4$ is hydrogen.

Still more preferably, the amine fluxing agent used in the amine fluxing composition of the present invention is according to formula I; wherein $R^1$, $R^2$, $R^3$ and $R^4$ are independently selected from a hydrogen, a —$CH_2CH(OH)R^{18}$ and a —$CH_2CH(OH)CH_2$—O—$R^{18}$ group; wherein $R^{18}$ is selected from a hydrogen, a $C_{1-28}$ alkyl group, a $C_{3-28}$ cycloalkyl group, a $C_{6-15}$ aryl group, a $C_{7-28}$ arylalkyl group and a $C_{7-28}$ alkylaryl group (preferably, wherein $R^{18}$ is selected from a $C_{5-10}$ alkyl group, a $C_{6-15}$ aryl group and a $C_{7-15}$ alkylaryl group; most preferably wherein $R^{18}$ is selected from a $C_8$ alkyl group, a $C_7$ alkylaryl group and a $C_{10}$ naphthyl group); wherein $R^7$ and $R^8$ are independently selected from a $C_{1-4}$ alkyl group and a $C_{1-4}$ hydroxy alkyl group (more preferably wherein $R^7$ and $R^8$ are independently selected from a methyl group and a hydroxy methyl group; most preferably wherein $R^7$ and $R^8$ are both a methyl group); wherein $R^{10}$ and $R^{11}$ are independently selected from a $C_{1-4}$ alkyl group and a $C_{1-4}$ hydroxy alkyl group (more preferably wherein $R^{10}$ and $R^{11}$ are independently selected from a methyl group and a hydroxy methyl group; most preferably wherein $R^{10}$ and $R^{11}$ are both a methyl group); and, wherein $R^9$ is selected from a hydrogen, a $C_{1-10}$ alkyl group, a $C_{1-10}$ hydroxyalkyl group, a phenyl group, a hydroxyphenyl group, a $C_{7-10}$ alkylaryl group, a $C_{7-10}$ arylalkyl group and a naphthyl group (more preferably wherein $R^9$ is selected from a hydrogen, a $C_{1-4}$ alkyl group, a $C_{1-4}$ hydroxyl alkyl group, a phenyl group, a hydroxyl phenyl group, a $C_7$ alkylaryl group and a $C_7$ arylalkyl group; most preferably wherein $R^9$ is selected from a methyl group and a phenyl group). Preferably, zero to three of $R^1$, $R^2$, $R^3$ and $R^4$ is(are) hydrogen. More preferably, one to three of $R^1$, $R^2$, $R^3$ and $R^4$ is(are) hydrogen. Still more preferably, two to three of $R^1$, $R^2$, $R^3$ and $R^4$ are hydrogen. Yet still more preferably, two of $R^1$, $R^2$, $R^3$ and $R^4$ are hydrogen. Most preferably, one of $R^1$ and $R^2$ is hydrogen and one of $R^3$ and $R^4$ is hydrogen.

Most preferably, the amine fluxing agent used in the amine flux composition of the present invention is according to formula I; wherein $R^1$, $R^2$, $R^3$ and $R^4$ are independently selected from a hydrogen, a —$CH_2CH(OH)R^{18}$ and a —$CH_2CH(OH)CH_2$—O—$R^{18}$ group; wherein $R^{18}$ is selected from a hydrogen, a —$CH_2CH(OH)R^{18}$ and a —$CH_2CH(OH)CH_2$—O—$R^{18}$ group; wherein $R^{18}$ is selected from a hydrogen, a $C_{1-28}$ alkyl group, a $C_{3-28}$ cycloalkyl group, a $C_{6-16}$ aryl group, a $C_{7-28}$ arylalkyl group and a $C_{7-28}$ alkylaryl group (preferably, wherein $R^{18}$ is selected from a $C_{5-10}$ alkyl group, a $C_{6-16}$ aryl group and a $C_{7-15}$ alkylaryl group; more preferably wherein $R^{18}$ is selected from a $C_8$ alkyl group, a $C_7$ alkylaryl group, a naphthyl group, a biphenyl group and a substituted $C_{12-16}$ biphenyl group; most preferably, wherein $R^{18}$ is selected from a $C_8$ alkyl group, a $C_7$ alkylaryl group and a naphthyl group); wherein $R^7$ and $R^8$ are both a methyl group; wherein $R^{10}$ and $R^{11}$ are both a methyl group; and, wherein $R^9$ is selected a methyl group and a phenyl group. Preferably, zero to three of $R^1$, $R^2$, $R^3$ and $R^4$ is(are) a hydrogen. More preferably, one to three of $R^1$, $R^2$, $R^3$ and $R^4$ is(are) hydrogen. Still more preferably, two to three of $R^1$, $R^2$, $R^3$ and $R^4$ are hydrogen. Yet still more preferably, two of $R^1$, $R^2$, $R^3$ and $R^4$ are hydrogen. Most preferably, $R^1$ and $R^3$ are hydrogen; and, $R^2$ and $R^4$ are selected from a —$CH_2CH(OH)R^{18}$ and a —$CH_2CH(OH)CH_2$—O—$R^{18}$ group.

The amine flux composition of the present invention optionally further comprises a solvent. Solvent is optionally included in the amine flux composition of the present invention to facilitate delivery of the amine fluxing agent to the surface, or surfaces, to be soldered. Preferably, the amine flux composition contains 8 to 95 wt % solvent. Solvent used in the amine flux composition of the present invention is preferably an organic solvent selected from hydrocarbons (e.g., dodecane, tetradecane); aromatic hydrocarbons (e.g., benzene, toluene, xylene, trimethylbenzene, butyl benzoate, dodecylbenzene); ketones (e.g., methyl ethyl ketone, methyl isobutyl ketone, cyclohexanone); ethers (e.g., tetrahydrofuran, 1,4-dioxaneandtetrahydrofuran, 1,3-dioxalane, dipropylene glycol dimethyl ether); alcohols (e.g., 2-methoxyethanol, 2-butoxyethanol, methanol, ethanol, isopropanol, α-terpineol, benzyl alcohol, 2-hexyldecanol,); esters (e.g., ethyl acetate, ethyl lactate, butyl acetate, diethyl adipate, diethyl phthalate, diethylene glycol monobutyl acetate, ethyl lactate, methyl 2-hydroxyisobutyrate, propylene glycol monomethyl ether acetate); and, amides (e.g., N-methylpyrrolidone, N,N-dimethylformamide and N,N-dimethylacetamide); glycol derivatives (e.g., cellosolve, butyl cellosolve); glycols (e.g., ethylene glycol; diethylene glycol; dipropylene glycol; triethylene glycol; hexylene glycol; 1,5-pentanediol); glycol ethers (e.g., propylene glycol monomethyl ether, methyl carbitol, butyl carbitol, triethylene glycol monomethyl ether, triethylene glycol dimethyl ether, tetraethylene glycol dimethyl ether, diethylene glycol monomethyl ether, diethylene glycol monobutyl ether, diethylene glycol monohexyl ether, ethylene glycol monophenyl ether, diethylene glycol monophenyl ether, diethylene glycol-2-ethylhexyl ether,); and petroleum solvents (e.g., petroleum ether, naptha). More preferably, the solvent used in the amine flux composition of the present invention is an organic solvent selected from methyl ethyl ketone; 2-propanol; propylene glycol monomethyl ether; propylene glycol monomethyl ether acetate; ethyl lactate and methyl 2-hydroxy isobutyrate. Most preferably, the solvent used in the amine flux composition of the present invention is propylene glycol monomethyl ether.

The amine flux composition of the present invention optionally further comprises a thickening agent. Preferably, the amine flux composition contains 0 to 30 wt % thickening agent. Thickening agent used in the amine flux composition of the present invention can be selected from non-curing resin materials (i.e., <2 reactive functional groups per molecule), such as, for example, a non-curing novolac resin.

The amine flux composition of the present invention optionally further comprises a thixotropic agent. Preferably, the amine flux composition contains 1 to 30 wt % thixotropic agent. Thixotropic agent used in the amine flux composition of the present invention can be selected from fatty acid amides (e.g., stearamide, hydroxystearic acid bisamide); fatty acid esters (e.g., castor wax, beeswax, carnauba wax); organic thixotropic agents (e.g., polyethylene glycol, polyethylene oxide, methyl cellulose, ethyl cellulose, hydroxyethyl cellulose, hydroxypropyl cellulose, diglycerine monooleate, deglycerine laurate, decaglycerine oleate, diglycerine monolaurate, sorbitan laurate); inorganic thixotropic agents (e.g., silica powders, kaolin powders). Preferably, the thixotropic agent used is selected from a polyethylene glycol and a fatty acid amide.

The amine flux composition of the present invention optionally further comprise an inorganic filler. Inorganic fillers can be selected from alumina, aluminum hydroxide, aluminosilicate, cordierite, lithium aluminum silicate, magnesium aluminate, magnesium hydroxide, clay, talc, antimony trioxide, antimony pentoxide, zinc oxide, colloidal silica, fused silica, glass powder, quartz powder and glass microspheres.

The amine flux composition of the present invention optionally further comprises an antioxidant. Preferably, the amine flux composition of the present invention contains 0.01 to 30 wt % antioxidant.

The amine flux composition of the present invention optionally further comprises an additive selected from matting agents, coloring agents, defoaming agents, dispersion stabilizers, chelating agents, thermoplastic particles, UV impermeable agents, flame retardants, leveling agents, adhesion promoters and reducing agents.

The amine flux composition of the present invention preferably comprises (consists essentially of), as an initial component: 3.99 to 100 wt % of an amine fluxing agent represented by formula I. Preferably, the amine flux composition of the present invention comprises (consists essentially of), as initial components: 3.99 to 100 wt % of an amine fluxing agent represented by formula I, 0 to 95 wt % (more preferably 8 to 95 wt %) of a solvent, 0 to 30 wt % thickening agent, 0 to 30 wt % (more preferably 1 to 30 wt %) of a thixotropic agent, and 0 to 30 wt % (more preferably 0.01 to 30 wt %) of an antioxidant.

The amine flux composition of the present invention can be used in, for example, the production of electronic components, electronic modules and printed circuit boards. The amine flux composition can be applied to the surface(s) to be soldered by any conventional technique including, for example, liquid spray techniques, liquid foaming techniques, pick and dip techniques and wave techniques or any other conventional technique capable of dispensing a liquid or semisolid onto a silicon die or substrate.

The amine flux composition of the present invention optionally further comprises a solder powder; wherein the amine flux composition is a solder paste. Preferably, the solder powder is an alloy selected from Sn/Pb, Sn/Ag, Sn/Ag/Cu, Sn/Cu, Sn/Zn, Sn/Zn/Bi, Sn/Zn/Bi/In, Sn/Bi and Sn/In (preferably wherein the solder powder is an alloy selected from 63 wt % Sn/37 wt % Pb; 96.5 wt % Sn/3.5 wt % Ag; 96 wt % Sn/3.5 wt % Ag/0.5 wt % Cu; 96.4 wt % Sn/2.9 wt % Ag/0.5 wt % Cu; 96.5 wt % Sn/3 wt % Ag/0.5 wt % Cu; 42 wt % Sn/58 wt % Bi; 99.3 wt % Sn/0.7 wt % Cu; 91 wt % Sn/9 wt % Zn and 89 wt % Sn/8 wt % Zn/3 wt % Bi).

The solder paste preferably comprises: 1 to 50 wt % (more preferably 5 to 30 wt %, most preferably 5 to 15 wt %) of an amine fluxing agent and 50 to 99 wt % of a solder powder. The solder paste can be compounded by conventional techniques, for example, by kneading and mixing the solder powder with the amine fluxing agent using conventional equipment for such operations.

The solder paste can be used in, for example, the production of electronic components, electronic modules and printed circuit boards. The solder paste can be applied to the surface(s) to be soldered by any conventional technique including, for example, printing the solder paste through a conventional solder mask using a solder printer or screen printer.

The amine fluxing agent used in the amine flux composition of the present invention can be prepared using conventional synthesis techniques well known to those of ordinary skill in the art.

The method of applying solder to an electrical contact of the present invention comprises: providing an electrical contact; providing an amine flux composition of the present invention; applying the amine flux composition to the electrical contact; providing a solder; melting the solder; and, displacing the amine flux composition applied to the electrical contact with the molten solder; wherein the molten solder makes physical contact with the electrical contact and bonds to the electrical contact. In the method, the molten solder desirably comes into intimate contact with the electrical contact to facilitate formation of a metallic bond between the solder material and the electrical contact, providing a good mechanical and electrical bond between the solder and the electrical contact. Any conventional soldering technique can be used in the method of the present invention. For example, a soldering bit or iron can be used to heat the electrical contact and the solder to a temperature above the melting point temperature for the solder. A soldering bath can be used, wherein solder in a liquid state is transferred to the electrical contact through immersion of the electrical contact into the molten solder. Conventional wave soldering techniques can be implemented. Also, reflow soldering techniques can also be used, wherein solder previously deposited onto a second electrical contact is brought into proximity with the first electrical contact and heated to a temperature above the melting point temperature of the solder, wherein the solder melts and reflows, coming into contact with both the first electrical contact and the second electrical contact, forming an electrical contact between the first electrical contact and the second electrical contact.

The method of applying solder to an electrical contact of the present invention can optionally be part of a flip chip soldering process, wherein a semiconductor chip is mounted onto a printed circuit board, wherein the semiconductor chip comprises a plurality of first electrical contacts and wherein the printed circuit board comprises a plurality of second electrical contacts. In such flip chip method, the amine flux composition of present invention is applied to either one, or both, of the plurality of first electrical contacts and the plurality of second electrical contacts to facilitate solder bonding of the plurality of first electrical contacts to the plurality of second electrical contacts to form electrical inter connects. Preferably, the flip chip solder process further comprises an under fill step wherein a thermosetting resin is provided to encapsulate the electrical inter connects. Most preferably, the thermosetting resin is an epoxy resin.

Some embodiments of the present invention will now be described in detail in the following Examples.

EXAMPLE 1

Synthesis of Amine Fluxing Agent

A 2,6-diamino-2,5,6-trimethylheptan-3-ol amine fluxing agent was prepared using the following procedure. First, a 2,5,6-trimethyl-2,6-dinitroheptan-3-ol intermediate was prepared using the following synthesis method

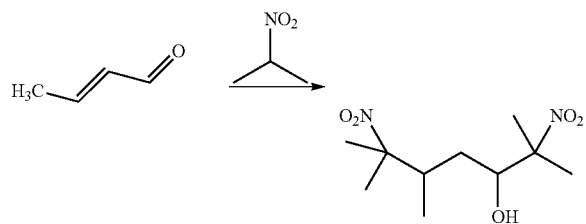

Specifically, a three neck round bottom flask was equipped with a stir bar, a thermocouple, a dropping funnel capped with a nitrogen inlet and a condenser. The flask was then charged with 2-nitropropane (50 g, 0.56 mols, 5.0 equivalents) and a catalytic amount of 1,8-diazabicyclo[5.4.0]undec-7-ene. The contents of the flask were then stirred under nitrogen for thirty minutes. Then crotonaldehyde (7.9 g, 9.2 mL, 0.112 moles, 1.0 equivalent) was added to the flask drop-wise over a period of twenty minutes. The contents of the flask were then stirred under nitrogen for 5-6 hours, during which a white solid was observed to precipitate from the solution. At this point, GC analysis showed the absence of any crotonaldehyde in the reaction mixture. The contents of the flask were allowed to stir overnight under nitrogen. The precipitate was then vacuum filtered from the solution and was washed thoroughly with water yielding a white solid. The intermediate solid was air dried, followed by vacuum drying at 45° C. The total yield of the desired intermediate dinitro alcohol was 72% (27.8 g). Nuclear magnetic resonance testing ("NMR") and liquid chromatography ("LC") showed that the intermediate was > 99% pure.

Second, the product 2,6-diamino-2,5,6-trimethylheptan-3-ol amine fluxing agent was then prepared from the intermediate dinitro alcohol using the following synthesis method

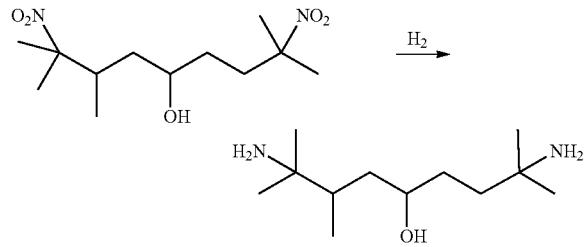

Specifically, 25 g of the intermediate dinitro alcohol was dissolved in 200 mL methanol with 14.2 g of RaNi 3111 as a catalyst. The mixture was then hydrogenated in an autoclave at 60° C. under 4,137 kPa (600 psi) of hydrogen pressure. After workup which included filtration of the catalyst and removal of methanol, 11 g (59% yield) of a low viscosity liquid product was obtained. NMR and gas chromatograph-mass spectroscopy ("GC-MS") analysis confirmed the presence of the desired product 2,6-diamino-2,5,6-trimethylheptan-3-ol amine fluxing agent. Chemical ionization mass spectroscopy (CI-MS) showed [M+H]=189 and GC analysis showed that the purity of the product to be 94%. The boiling point of the material was 125° C. to 135° C. at 0.68 kPa (5.1 torr). $^{13}$C NMR (CDCl$_3$): δ 16.8, 25.2, 27.9, 30.8, 34.7, 42.2, 51.8, 52.8 and 77.3 ppm.

EXAMPLE 2

Synthesis of Amine Fluxing Agent

A 2,6-diamino-2,6-dimethyl-5-phenylheptan-3-ol amine fluxing agent was prepared using the following procedure. First, a 2,6-dimethyl-2,6-dinitro-5-phenylheptan-3-ol intermediate was prepared using the following synthesis method

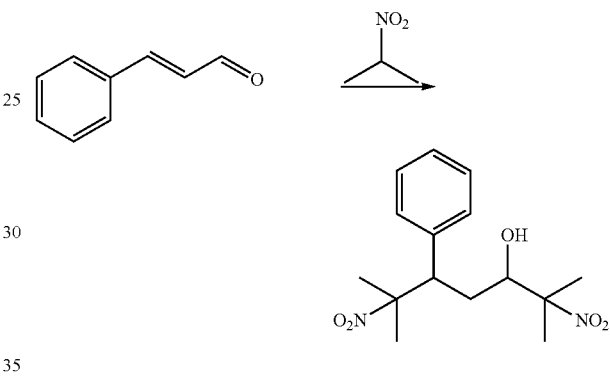

Specifically, a three neck round bottom flask was equipped with a stir bar, a thermocouple, a dropping funnel capped with a nitrogen inlet and a condenser. The flask was then charged with 2-nitropropane (101.1 g, 1.14 mols, 6.0 equivalents) and a catalytic amount of 1,8-diazabicyclo[5.4.0]undec-7-ene ("DBU"). The contents of the flask were then stirred under nitrogen for twenty minutes. Then trans-cinnamaldehyde (25.0 g, 0.19 moles, 1.0 equivalent) was added to the flask drop-wise over a period of twenty minutes. During the addition of the trans-cinnamldehyde, an exotherm of approximately 22° C. was observed. Following the complete addition of the trans-cinnamaldehyde, the flask contents were heated to 50° C. and maintained at that temperature for 4 hours. The mixture was then allowed to cool to room temperature. When the flask contents reached 36.8° C., a pale yellow solid formed out of the solution. The flask contents were then filtered through a Buchner funnel and the recovered intermediate diamino alcohol powder was washed thoroughly with pentane and ether. The intermediate diamino alcohol powder was then left to dry under vacuum for 1 hour. The total yield of the desired diamino alcohol intermediate was 62% (36 g). NMR analysis showed that the diamino alcohol intermediate was >99% pure. $^1$H NMR (CDCl$_3$): δ 1.45-2.27 (m, 15H), 3.52-3.54 (m, 1H), 3.67-3.74 (m, 1H), 7.17-7.34 (m, 5H). $^{13}$C NMR (CDCl$_3$): δ 20.8, 22.4, 23.2, 25.8, 31.3, 50.3, 72.9, 91.5, 91.6, 128.1, 128.7, 129.4, 136.6 ppm.

Second, the product 2,6-diamino-2,6-dimethyl-5-phenyl-heptane-3-ol amine fluxing agent was then prepared from the dinitro alcohol intermediate using the following synthesis method

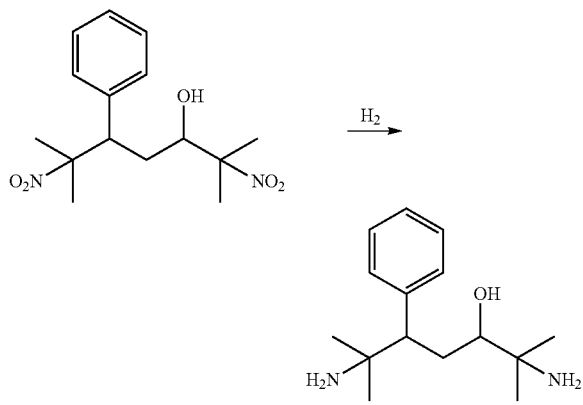

Specifically, 50 g of the dinitro alcohol intermediate was dissolved in 300 mL methanol with 24.3 g of RaNi 3111 as a catalyst. The mixture was then hydrogenated in an autoclave at 60° C. under 4137 kPa (600 psi) of hydrogen pressure. After workup which included filtration of the catalyst and removal of methanol, 40 g (68% yield) of a high viscosity liquid product was obtained. NMR and gas chromatograph-mass spectroscopy ("GC-MS") analysis confirmed the presence of the desired product 2,6-diamino-2,6-dimethyl-5-phenylheptane-3-ol amine fluxing agent. Chemical ionization mass spectroscopy (CI-MS) showed [M+H]=251 and GC analysis showed that the purity of the product to be 78% straight from the autoclave. The rest of the material present appeared to be the mono adduct obtained from the reversal of the Henry reaction. The product was then purified to 96.2% purity by vacuum distillation. The boiling point of the purified product was determined to be 150° C. to 160° C. at 0.67 kPa (5.0 torr). $^1$H NMR (CDCl$_3$): δ 0.91-0.99 (m, 12H), 1.67-1.81 (m, 3H), 2.71-2.76 (m, 2H), 7.08-7.23 (m, 5H). $^{13}$C NMR (CDCl$_3$): δ 24.6, 27.9, 28.3, 29.8, 31.6, 51.8, 52.6, 54.2, 75.9, 126.3, 127.8, 129.4, 142.0 ppm.

EXAMPLE 3

Synthesis of Amine Fluxing Agent

An amine fluxing agent having the formula

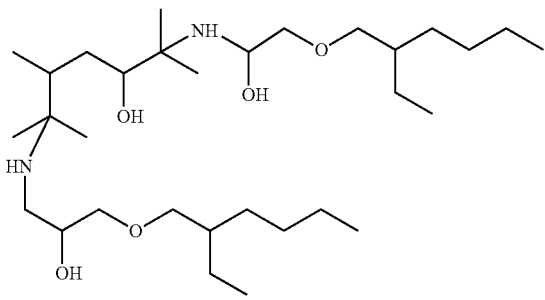

was prepared using the following procedure. Specifically, into a reaction vessel with a stir bar, (0.05 mol) of the product of Example 1 was added. The reaction vessel was then placed on a hotplate with magnetic stirring capability. The reaction vessel was then inerted with nitrogen and (0.1 mol) of 2-ethylhexyl glycidyl ether (available from Momentive Performance Materials) was then added to the reaction vessel at ambient temperature, with stirring. The set point temperature on the hot plate was then raised to 75° C. and the contents of the reaction vessel were allowed to continue stirring for two (2) hours. The set point temperature of the hot plate was then raised to 140° C. and the contents of the reaction vessel were allowed to continue stirring for two (2) more hours. The set point temperature of the hot plate was then reduced to 80° C. and a vacuum was pulled on the reaction vessel, reducing the pressure in the vessel to 30 mm Hg. The contents of the reaction vessel were allowed to continue stirring under these conditions for another two (2) hours to provide the product fluxing agent. The percent weight loss from the product fluxing agent upon heating to 250° C. was measured by thermogravimetric analysis (TGA) using a temperature ramp of 10° C./min starting at 25° C. The measured weight loss (WL) for the product fluxing agent was 9 wt %.

EXAMPLE 4

Synthesis of Amine Fluxing Agent

An amine fluxing agent having the formula

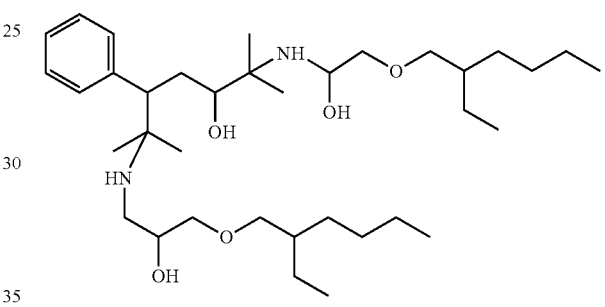

was prepared using the following procedure. Specifically, into a reaction vessel with a stir bar, (0.05 mol) of the product of Example 2 was added. The reaction vessel was then placed on a hotplate with magnetic stirring capability. The reaction vessel was then inerted with nitrogen and (0.1 mol) of 2-ethylhexyl glycidyl ether (available from Momentive Performance Materials) was then added to the reaction vessel at ambient temperature, with stirring. The set point temperature on the hot plate was then raised to 75° C. and the contents of the reaction vessel were allowed to continue stirring for two (2) hours. The set point temperature of the hot plate was then raised to 140° C. and the contents of the reaction vessel were allowed to continue stirring for two (2) more hours. The set point temperature of the hot plate was then reduced to 80° C. and a vacuum was pulled on the reaction vessel, reducing the pressure in the vessel to 30 mm Hg. The contents of the reaction vessel were allowed to continue stirring under these conditions for another two (2) hours to provide the product fluxing agent. The percent weight loss from the product fluxing agent upon heating to 250° C. was measured by thermogravimetric analysis (TGA) using a temperature ramp of 10° C./min starting at 25° C. The measured weight loss (WL) for the product fluxing agent was 5 wt %.

EXAMPLE 5

Evaluation of Fluxing Capability

The fluxing capability of amine flux compositions prepared according to Examples 3-4 was evaluated and compared with a hydroxystearic acid reference material using the following procedure. In each evaluation, a copper coupon was used as an electrical contact to be soldered. The surface to be soldered on each of the copper coupons was pretreated by: (1) first polishing with fine sand paper (600 grit), (2) then cleaning with a 5% ammonium persulfate solution, (3) then rinsing with deionized water, (4) then dipping in a 1% benzotriazole solution for 30 seconds, and (5) then blow drying with nitrogen. Following pretreatment of the copper coupons, a small drop of each one the amine flux compositions was individually dispensed onto the surface to be soldered of one of the copper coupons. Four 0.381 mm diameter balls of a lead-free solder (95.5 wt % Sn/4.0 wt % Ag/0.5 wt % Cu) were placed into the drop of amine flux composition on each of the copper coupons. The melting range of the lead-free solder used is 217 to 221° C. The copper coupons were then placed on a hotplate that was preheated to 145° C. and held there for two (2) minutes. The copper coupons were then placed on another hotplate preheated to 260° C. and held there until the solder reached reflow conditions (45 sec. to 3 min. depending on the amine flux composition present). The copper coupons were then removed from the heat and evaluated by (a) the extent of fusion and coalescence of the originally placed four solder balls, (b) the size of the resulting coalesced solder to assess the flow and spread and (c) the bonding of the solder to the surface of the copper coupon. A scale of 0 to 4 was used to describe the amine fluxing capability of the amine flux compositions and the hydroxystearic acid reference material, as follows:

0=no fusion between solder drops and no solder bonding to copper coupon;
1,2=partial to complete fusion between solder drops, but no solder bonding to copper coupon;
3=complete fusion between solder drops, but minimal solder spread and flow;
4=complete fusion between solder drops, good solder spread and flow over surface of copper coupon and solder bonding to the copper coupon.

The result of the evaluation of the amine flux compositions is provided in TABLE 1

TABLE 1

| Amine flux Composition | Evaluation Result |
|---|---|
| Example 3 | 4 |
| Example 4 | 4 |
| Reference material (hydroxystearic acid) | 4 |

We claim:
1. An amine flux composition comprising, as an initial component:
an amine fluxing agent represented by formula I:

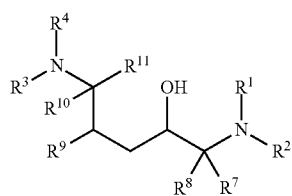

(I)

wherein $R^1$, $R^2$, $R^3$ and $R^4$ are independently selected from a hydrogen, a substituted $C_{1-80}$ alkyl group, an unsubstituted $C_{1-80}$ alkyl group, a substituted $C_{7-80}$ arylalkyl group and an unsubstituted $C_{7-80}$ arylalkyl group; wherein $R^7$ and $R^8$ are independently selected from a $C_{1-20}$ alkyl group, a substituted $C_{1-20}$ alkyl group, a $C_{6-20}$ aryl group and a substituted $C_{6-20}$ aryl group or wherein $R^7$ and $R^8$, together with the carbon to which they are attached, form a $C_{3-20}$ cycloalkyl ring optionally substituted with a $C_{1-6}$ alkyl group; wherein $R^{10}$ and $R^{11}$ are independently selected from a $C_{1-20}$ alkyl group, a substituted $C_{1-20}$ alkyl group, a $C_{6-20}$ aryl group and a substituted $C_{6-20}$ aryl group or wherein $R^{10}$ and $R^{11}$, together with the carbon to which they are attached, form a $C_{3-20}$ cycloalkyl ring optionally substituted with a $C_{1-6}$ alkyl group; and, wherein $R^9$ is selected from a hydrogen, a $C_{1-30}$ alkyl group, a substituted $C_{1-30}$ alkyl group, a $C_{6-30}$ aryl group and a substituted $C_{6-30}$ aryl group.

2. The amine flux composition of claim 1, wherein the substitutions in the substituted $C_{1-80}$ alkyl group and the substituted $C_{7-80}$ arylalkyl group, from which $R^1$, $R^2$, $R^3$ and $R^4$ are selected, are selected from at least one of an —OH group, an —$OR^5$ group, a —$COR^5$— group, a —$COR^5$ group, a —$C(O)R^5$ group, a —CHO group, a —$COOR^5$ group, an —$OC(O)OR^5$ group, a —$S(O)(O)R^5$ group, a —$S(O)R^5$ group, a —$S(O)(O)NR^5_2$ group, an —$OC(O)NR^6_2$ group, a —$C(O)NR^6_2$ group, a —CN group, a —$N(R^6)$— group and a —$NO_2$ group; wherein $R^5$ is selected from a $C_{1-28}$ alkyl group, a $C_{3-28}$ cycloalkyl group, a $C_{6-15}$ aryl group, a $C_{7-28}$ arylalkyl group and a $C_{7-28}$ alkylaryl group; wherein $R^6$ is selected from a hydrogen, a $C_{1-28}$ alkyl group, a $C_{3-28}$ cycloalkyl group, a $C_{6-15}$ aryl group, a $C_{7-28}$ arylalkyl group and a $C_{7-28}$ alkylaryl group.

3. The amine flux composition of claim 1, wherein $R^1$, $R^2$, $R^3$ and $R^4$ are independently selected from a hydrogen, a —$CH_2CH(OH)R^{18}$ and a —$CH_2CH(OH)CH_2$—O—$R^{18}$ group; wherein $R^{18}$ is selected from a hydrogen, a $C_{1-28}$ alkyl group, a $C_{3-28}$ cycloalkyl group, a $C_{6-28}$ aryl group, a $C_{7-28}$ arylalkyl group and a $C_{7-28}$ alkylaryl group; wherein $R^7$ and $R^8$ are both a methyl group; wherein $R^{10}$ and $R^{11}$ are both a methyl group; and, wherein $R^9$ is selected a methyl group and a phenyl group; and wherein zero to three of $R^1$, $R^2$, $R^3$ and $R^4$ is(are) hydrogen.

4. The amine flux composition of claim 3, wherein zero to three of $R^1$, $R^2$, $R^3$ and $R^4$ is(are) hydrogen.

5. The amine flux composition of claim 1, further comprising a solvent, wherein the solvent is an organic solvent selected from hydrocarbons, aromatic hydrocarbons, ketones, ethers, alcohols, esters, amides, glycols, glycol ethers, glycol derivatives and petroleum solvents.

6. The amine flux composition of claim 1, further comprising at least one of:
an inorganic filler; a thixotropic agent; and an antioxidant.

7. The amine flux composition of claim 1, further comprising:
an additive selected from matting agents, coloring agents, defoaming agents, dispersion stabilizers, chelating agents, thermoplastic particles, UV impermeable agents, flame retardant and reducing agents.

8. The amine flux composition of claim 1, further comprising, as initial components:
0 to 95 wt % of a solvent,
0 to 30 wt % of a thickening agent,
0 to 30 wt % of a thixotropic agent, and
0 to 30 wt % of an antioxidant.

9. The amine flux composition of claim 1, further comprising: a solder powder.

10. A method of applying solder to an electrical contact, comprising:
providing an electrical contact;
providing an amine flux composition according to claim 1;

applying the amine flux composition to the electrical contact;
providing a solder;
melting the solder; and,
displacing the amine flux composition applied to the electrical contact with the molten solder;
wherein the molten solder makes physical contact with the electrical contact and bonds to the electrical contact.

* * * * *